(12) United States Patent
Bliss et al.

(10) Patent No.: US 6,910,482 B2
(45) Date of Patent: Jun. 28, 2005

(54) SELF-CALIBRATING SUPPLEMENTAL OXYGEN DELIVERY SYSTEM

(75) Inventors: Peter L. Bliss, Prior Lake, MN (US); Willard S. Davidson, Wabasha, MN (US)

(73) Assignee: Chart Inc., Burnsville, MN (US)

( * ) Notice: Subject to any disclaimer, the term of this patent is extended or adjusted under 35 U.S.C. 154(b) by 0 days.

(21) Appl. No.: 10/273,503

(22) Filed: Oct. 18, 2002

(65) Prior Publication Data

US 2003/0150455 A1 Aug. 14, 2003

Related U.S. Application Data

(60) Provisional application No. 60/335,428, filed on Oct. 19, 2001.

(51) Int. Cl.$^7$ ............................................. A61M 16/00
(52) U.S. Cl. ........................... 128/204.26; 128/205.24; 128/204.21; 128/204.18
(58) Field of Search ....................... 128/204.26, 204.29, 128/204.18, 204.22, 204.23, 202.22, 203.22, 207.18, 205.24

(56) References Cited

U.S. PATENT DOCUMENTS

| | | | |
|---|---|---|---|
| 4,054,133 A | | 10/1977 | Myers |
| 4,278,110 A | * | 7/1981 | Price et al. ................. 137/805 |
| 4,457,303 A | | 7/1984 | Durkan |
| 4,462,398 A | | 7/1984 | Durkan et al. |
| 4,484,578 A | | 11/1984 | Durkan |
| 4,519,387 A | | 5/1985 | Durkan et al. |
| 4,686,975 A | | 8/1987 | Naimon et al. |
| 4,706,664 A | * | 11/1987 | Snook et al. ............ 128/204.23 |
| 4,827,922 A | | 5/1989 | Champain et al. |
| 4,848,332 A | | 7/1989 | Champain |
| 4,932,402 A | * | 6/1990 | Snook et al. ............ 128/204.23 |
| 4,971,049 A | * | 11/1990 | Rotariu et al. ........... 128/204.21 |
| 5,099,836 A | | 3/1992 | Rowland et al. |
| 5,443,062 A | | 8/1995 | Hayes |
| 5,551,419 A | | 9/1996 | Froehlich et al. |
| 5,603,315 A | * | 2/1997 | Sasso, Jr. ............... 128/204.18 |
| 5,701,883 A | * | 12/1997 | Hete et al. .............. 128/204.26 |
| 5,720,276 A | * | 2/1998 | Kobatake et al. ......... 128/204.18 |
| 5,735,268 A | | 4/1998 | Chua et al. |
| 5,839,434 A | | 11/1998 | Enterline |
| 5,865,174 A | * | 2/1999 | Kloeppel ................ 128/204.23 |
| 5,881,722 A | * | 3/1999 | DeVries et al. .......... 128/204.21 |
| 6,000,396 A | * | 12/1999 | Melker et al. ........... 128/204.21 |
| 6,017,315 A | | 1/2000 | Starr et al. |
| 6,131,571 A | * | 10/2000 | Lampotang et al. ...... 128/204.21 |
| 6,164,276 A | * | 12/2000 | Bathe et al. ............ 128/202.22 |
| 6,192,884 B1 | * | 2/2001 | Vann et al. ............. 128/204.26 |
| 6,224,560 B1 | * | 5/2001 | Gazula et al. ............... 600/538 |
| 6,237,592 B1 | * | 5/2001 | Surjadi et al. .......... 128/204.21 |
| 6,378,520 B1 | * | 4/2002 | Davenport ............. 128/204.26 |
| 6,526,971 B2 | * | 3/2003 | Kellon ................. 128/204.28 |
| 6,539,940 B2 | * | 4/2003 | Zdrojkowski et al. . 128/204.23 |
| 6,575,164 B1 | * | 6/2003 | Jaffe et al. ............. 128/205.24 |
| 6,668,828 B1 | * | 12/2003 | Figley et al. ........... 128/204.18 |

\* cited by examiner

*Primary Examiner*—Henry Bennett
*Assistant Examiner*—Mital Patel
(74) *Attorney, Agent, or Firm*—DLA Piper Rudnick Gray Cary US LLP

(57) ABSTRACT

An on demand supplemental oxygen delivery system that is self-calibrating includes a tank containing a supply of oxygen and a nasal cannula through which the oxygen may be provided to a patient when the system solenoid valve is in the open condition. When the valve is in the closed condition, the cannula communicates with a pressure transducer via a transducer line. An orifice is formed in the line so that the pressure within the transducer line goes to atmospheric pressure when the valve is in the open condition. The pressure transducer reads the atmospheric pressure and directs it to a system controller where it is stored as a reference pressure.

20 Claims, 3 Drawing Sheets

SELF-CALIBRATING SUPPLEMENTAL OXYGEN DELIVERY SYSTEM

CLAIM OF PRIORITY

This application claims priority from U.S. Provisional Patent Application Ser. No. 60/335,428, filed Oct. 19, 2001 now abandoned.

BACKGROUND OF THE INVENTION

The present invention relates generally to systems for providing supplemental oxygen to patients and, more particularly, to oxygen conserving devices for such systems.

Respiratory diseases, such as bronchitis and emphysema, cause patients to suffer from deterioration of lung function. Health care providers often prescribe supplemental oxygen to such patients so that they can inhale the supplemental oxygen along with ambient atmospheric air in order to maintain a sufficient oxygen concentration level in the blood stream. The supplemental oxygen is provided by a system that stores or generates the oxygen and provides it to the patient via a nasal cannula.

In early supplemental oxygen delivery systems, oxygen was delivered on a continuous flow basis, albeit at a low, fixed flow rate, throughout the entire breathing cycle to the nose of the patient by a tube which interconnected a source of oxygen with a nasal cannula. Although such systems were effective, oxygen was lost to the ambient atmosphere since the continuous flow of oxygen was provided to the patient's nose regardless if the patient was inhaling or exhaling.

In response to the waste of oxygen associated with the earlier prior art supplemental oxygen delivery systems, more efficient prior art systems and devices were developed and implemented for delivery of supplemental oxygen to patients. These devices included oxygen conserving features. Such devices include those which provide oxygen "on demand" to the patient. "On demand" systems deliver oxygen to the patient after the beginning of the inhalation interval of the breathing cycle while no oxygen is delivered to the patient during any portion of the exhalation interval of the breathing cycle.

Examples of such prior art supplemental oxygen delivery devices are presented in U.S. Pat. Nos. 4,462,398 and 4,519,387, both to Durkan et al. In the device of these patents, a control circuit responsive to a sensor operates a valve to supply pulses of oxygen through a cannula to a patient when negative pressure indicating the initial stage of inhalation is detected by the sensor. The sensor may be a pressure-to-electric switch/pressure transducer. The pulse of gas delivered to the patient can have a preselected pulse profile.

U.S. Pat. No. 4,686,975 to Naimon et al. also discloses a supplemental respiratory device wherein small pressure changes within an airway are monitored so that gas is only supplied during patient inhalation. The nasal cannula leads from the airway to the sensing means which takes the form of a pressure transducer.

In the devices of the above patents, and other similar prior art devices and systems, it is advantageous to apply a commercially available pressure transducer. Such transducers are available from Honeywell Inc. of Morristown, N.J. (Micro Switch model 24 PC), Sensym of Milpitas, Calif. (model SX) and other manufacturers. Such pressure transducers are readily available, inexpensive, small and reliable.

In order to reliably identify the onset of patient inhalation, the pressure transducer must sense a pressure in the cannula of approximately −0.1 cm of water at atmospheric pressure. Pressure transducers have an associated drift due to time, temperature and applied pressure (hysteresis). As a result, to achieve the necessary pressure sensitivity, the pressure transducer must be accurately calibrated or zeroed at atmospheric pressure. The pressure transducers of the above paragraph, however, do not feature a built in reference to atmospheric pressure. Accordingly, the problem exists as to how to efficiently calibrate or zero the pressure transducer of an "on demand" supplemental oxygen delivery device.

Some prior art supplemental oxygen delivery devices, such as the Pulsair/DeVilbiss OMS 20, have an adjustable pressure transducer by which the set triggering point may be manually adjusted. The set triggering point is the pressure at which the device is triggered to deliver oxygen. Such devices, however, require periodic adjustment to assure consistent triggering without "auto-cycling." Auto-cycling occurs when the set trigger point is at or above atmospheric pressure.

Other prior art supplemental oxygen delivery devices, such as the AirSep Impulse Select, monitor an airway for a change in pressure instead of an absolute pressure level. This approach, however, carries with it the disadvantage that under some breathing conditions, the device might interpret a strong exhalation (decreasing expiratory flow) as the same as an inspiration (increasing inspiratory flow) as the slopes of the pressure profile waveforms for each are similar. As a result, the device may be triggered to deliver oxygen at an inappropriate time.

The pressure transducer of a supplemental oxygen delivery device may also be calibrated to an assumed atmospheric pressure when the device is powered on, as in the case of the DeVilbiss EX2000 device. Such an approach, however, may result in an incorrect reference pressure if the patient is breathing on the cannula when the device is turned on. An incorrect reference pressure causes the device to be difficult to trigger or the device may trigger, and thus deliver oxygen, at the wrong time.

Finally, prior art supplemental oxygen delivery devices such as the Transtracheal Systems DOC2000, DOC3000 and DeVilibiss EX2005 feature two valves. The first valve controls the delivery of oxygen to the patient. The second valve is used to vent the pressure transducer to atmospheric pressure while oxygen is being delivered to the patient. This allows the pressure transducer to be calibrated or zeroed to atmospheric pressure. While this approach is reliable, it has a high associated cost and power consumption because two valves are required.

Accordingly, it is an object of the present invention to provide a self-calibrating supplemental oxygen delivery system;

It is another object of the present invention to provide a supplemental oxygen delivery system that is reliable;

It is another object of the present invention to provide an "on demand" supplemental oxygen delivery system;

It is another object of the present invention to provide a supplemental oxygen delivery system that is cost effective to construct;

It is still another object of the present invention to provide a supplemental oxygen delivery system that is economical to operate.

SUMMARY OF THE INVENTION

The present invention is directed to a system for delivering supplemental oxygen, or other gases, to a patient. The system includes a tank containing oxygen and a nasal cannula through which oxygen gas from the tank may be provided to the patient. The system also includes a pressure transducer and a transducer line in communication with the pressure transducer. The transducer line is provided with an orifice. A 3-port two position solenoid valve is in communication with the nasal cannula and is adjustable between an open condition where the tank is in communication with the nasal cannula and a closed condition where the pressure transducer is in communication with the nasal cannula via the transducer line.

A controller is in communication with the pressure transducer and the valve. The pressure transducer senses atmospheric pressure in the transducer line due to the orifice when the valve is in the open condition and the sensed pressure is stored and used by the controller as a reference pressure. The valve is configured in the open condition by the controller when the pressure in the nasal cannula, as sensed by the pressure transducer when the valve is in the closed condition, drops below the reference pressure, such as when a patient inhales.

The following detailed description of embodiments of the invention, taken in conjunction with the appended claims and accompanying drawings, provide a more complete understanding of the nature and scope of the invention.

DESCRIPTION OF THE PREFERRED EMBODIMENTS

Figure 1A:
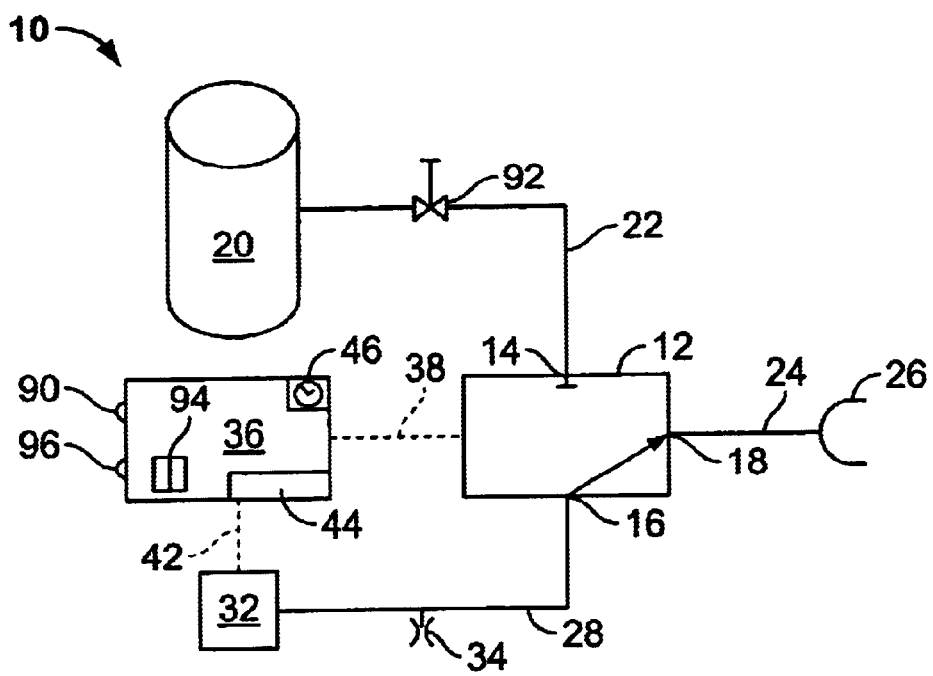
FIGS. 1A and 1B are schematics of an embodiment of the supplemental oxygen delivery system of the present invention with the system valve in the closed and open configurations, respectively.
Figure 1B:
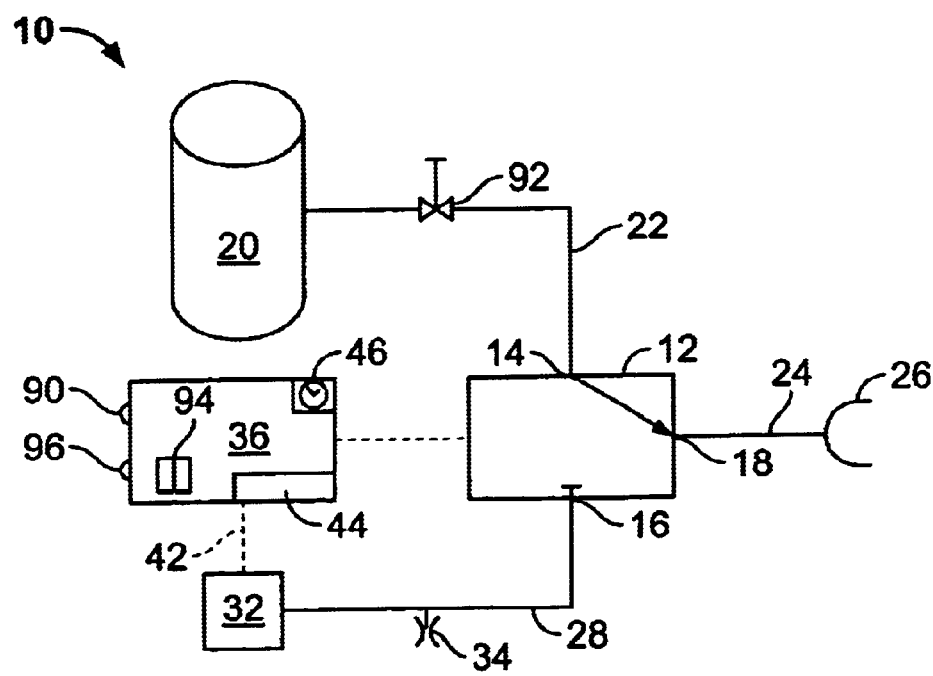

An embodiment of the supplemental oxygen delivery system of the invention is indicated in general at 10 in FIGS. 1A and 1B. As will be explained in greater detail below, FIG. 1A illustrates the system with its valve 12 in the closed condition or configuration so that oxygen is not being delivered to a patient. In contrast, FIG. 1B illustrates the system with its valve 12 in the open condition or configuration so that oxygen is being delivered to a patient.

As illustrated in FIGS. 1A and 1B, the system features a 3-port two position solenoid-actuated poppet valve 12 having two input ports 14 and 16 and one outlet port 18. While a solenoid valve is described herein, other types of valves known in the art may be alternatively used. Inlet port 14 communicates with a pressurized gas source, such as a tank 20 containing oxygen, via a line 22. Depending upon the particular environment of use, the pressurized gas source may be a portable tank or a wall supply, as in a hospital. Tank 20 may be a high pressure (for example, 2000 psi) cylinder with a suitable pressure regulator to maintain a supply of 20–50 psig. Tank 20 may alternatively be an insulated cylinder containing liquid oxygen at a pressure of approximately 20 psi. As used herein, unless otherwise indicated, any fluid conveying means, such as a tube, hose, duct, pipe or channel, or other closed fluid conduit, is referred to as a line. The lines, for example, may be formed in a manifold or from elastomeric tubing.

The outlet port 18 of valve 12 communicates via line 24 with a nasal cannula 26 connected to a patient (not shown). While a single hose nasal cannula is illustrated in FIGS. 1A and 1B and described herein, it is to be understood that alternative devices for providing the gas to the patient known in the art, such as an oxygen mask, for example, may be employed instead.

Inlet port 16 of valve 12 communicates via transducer line 28 with a pressure transducer 32. As described earlier, suitable pressure transducers are available from Honeywell Inc. of Morristown, N.J. (Micro Switch model 24 PC), Sensym of Milpitas, Calif. (model SX) and other manufacturers. An orifice 34 is formed in the transducer line 28. An electronic control system or controller 36 controls the configuration of valve 12 via electrical lead 38 based upon the information received from the pressure transducer 32 via electrical lead 42. The controller or control system may take the form of a microcomputer, microprocessor or other programmable electronic device.

FIG. 1A illustrates valve 12 in the closed condition. When valve 12 is in the closed condition, inlet port 14 is closed while inlet port 16 is open. Outlet port 18 always remains open. As a result, pressure transducer 32 is in communication with the patient cannula 26. When the patient inhales, the pressure transducer detects the pressure drop below atmospheric pressure in the patient cannula via lines 24 and 28 and, when a predetermined pressure is reached, sends a signal to the control system 36 via lead 42. The control system then reconfigures the valve 12 in the open condition, illustrated in FIG. 1B, where port 16 is closed and port 14 is open. As a result, oxygen from tank 20 is provided to the patient cannula 26 via lines 22 and 24.

As illustrated in FIG. 1B, when the valve 12 is in the open condition, port 16 is closed and the pressure transducer 32 measures the pressure within transducer line 28. Notably, transducer line 28 returns to atmospheric pressure because of the small orifice 34 formed therein. The orifice communicates with the transducer line and with the atmosphere. Thus, the transducer 32 is able to measure the atmospheric pressure each time valve 12, and thus port 16, closes.

Importantly, the orifice 34 is sized sufficiently small so as not to interfere with the operation of the transducer 32 in detecting the pressure drop at the commencement of patient inhalation when the valve is closed. However, the orifice is sufficiently large to allow the transducer line 28 to return to atmospheric pressure during patient inhalation when the valve is open. Testing has shown that an orifice of approximately 0.010 inches in diameter works well. The orifice may be formed in the transducer line 28 directly. Alternatively, a "tee" fitting, or some other component, such as a metal tube, 34 having the orifice formed therein may be inserted in series within transducer line 28.

A sample and hold circuit 44 is included within the control system 36 to "read" the value of the pressure transducer 32 and save it for future reference. More specifically, as will be explained in greater detail below with reference to FIG. 3, the sample and hold circuit receives the pressure detected by the transducer 32 in line 28 when the valve 12 is configured in the open condition. As a result, atmospheric pressure is read by the transducer 32 and stored in the sample and hold circuit 44 of the control system 36 as a reference pressure ($P_{reference}$). The sample and hold circuit 44 of FIGS. 1A and 1B may be accomplished in a variety of ways including with discreet components, a specialty integrated circuit or a microprocessor.

The newly-generated reference pressure is compared by the control system to the pressure detected by the pressure transducer in cannula 26 when the valve 12 is closed. The control system 36 opens valve 12 when the pressure detected within the cannula drops to some level below the reference pressure. As a result, the pressure transducer and control system are effectively calibrated or zeroed to atmospheric pressure.

The control system 36 features a timer 46 so that valve 12, once opened, remains opened for a predetermined period of time. When the time period expires, the control system automatically closes valve 12 so that port 14 is once again closed and port 16 is once again open. As such, the system is configured once again so that pressure transducer 32 may sense when the patient inhales.

Figure 2:
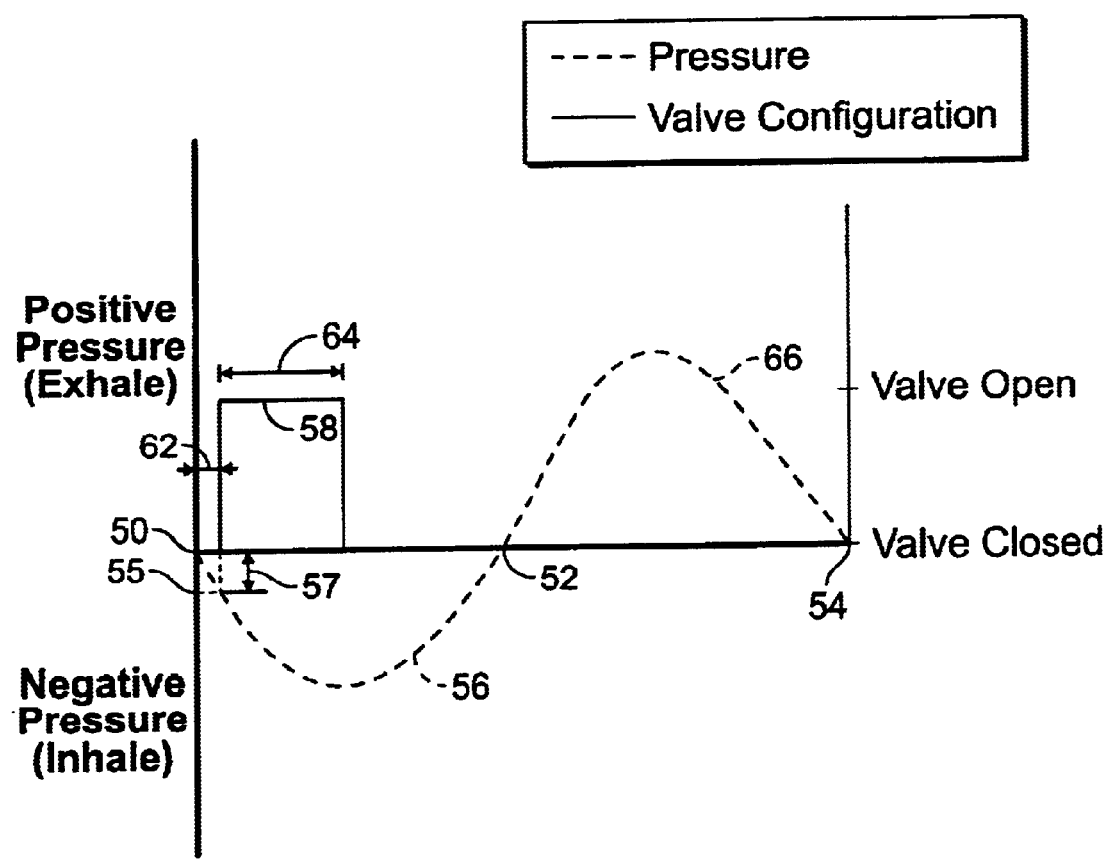
FIG. 2 is a graph illustrating the pressure profile of a breathing cycle of a patient including the inhalation and exhalation intervals with the corresponding configuration of the valve of the supplemental oxygen delivery system of FIGS. 1 A and 1B superimposed thereon.

A breathing cycle is graphed in FIG. 2 and is useful to illustrate the operation of the system of FIGS. 1A and 1B. The horizontal axis of FIG. 2 represents time (increasing from left to right) while the left vertical axis represents the pressure in the cannula 26 of FIGS. 1A and 1B. Point 50 corresponds to a time of zero seconds and atmospheric pressure. The right vertical axis represents the configuration or condition of valve 12 of FIGS. 1A and 1B.

The breathing cycle commences when the patient begins to inhale and terminates when a patient finishes exhaling. As a result, a breathing cycle consists of an inhalation interval and an exhalation interval. With reference to FIG. 2, the inhalation interval occurs between the time indicated at point 50 (zero seconds) and the time indicated at point 52. The exhalation cycle occurs between the time indicated at point 52 and the time indicated at point 54. During the inhalation cycle, the pressure within the nasal cannula drops as indicated by curve 56. When the pressure within the cannula drops to a predetermined pressure 55 that is below atmospheric pressure by offset pressure $P_{offset}$, indicated at 57 in FIG. 2, the valve 12 opens, as indicated by line 58. $P_{offset}$ may be, for example, in the range of 0.1–0.2 cm of water. The minute portion of time indicated at 62 represents the time required for the pressure within the nasal cannula to drop in response to the patient inhalation and for the electronic circuit and valve to respond.

The valve 12 of FIGS. 1A and 1B remains open for the period of time indicated by 64 in FIG. 2 during which a pulse or dose of oxygen is provided to the nasal cannula, and thus, to the patient. The period of time 64 corresponds to the setting of the timer 46 of FIGS. 1A and 1B. As an example only, the time may be in the range of approximately 0.05 to 0.6 seconds. After the valve closes, the patient completes the inhalation interval, and begins the exhalation interval, at the time indicated by point 52 in FIG. 2. As illustrated by curve 66, the pressure within the nasal cannula increases above atmospheric pressure as the patient exhales. Upon completion of the exhalation interval at the time indicated by point 54, the breathing cycle is completed and then repeated.

Figure 3:
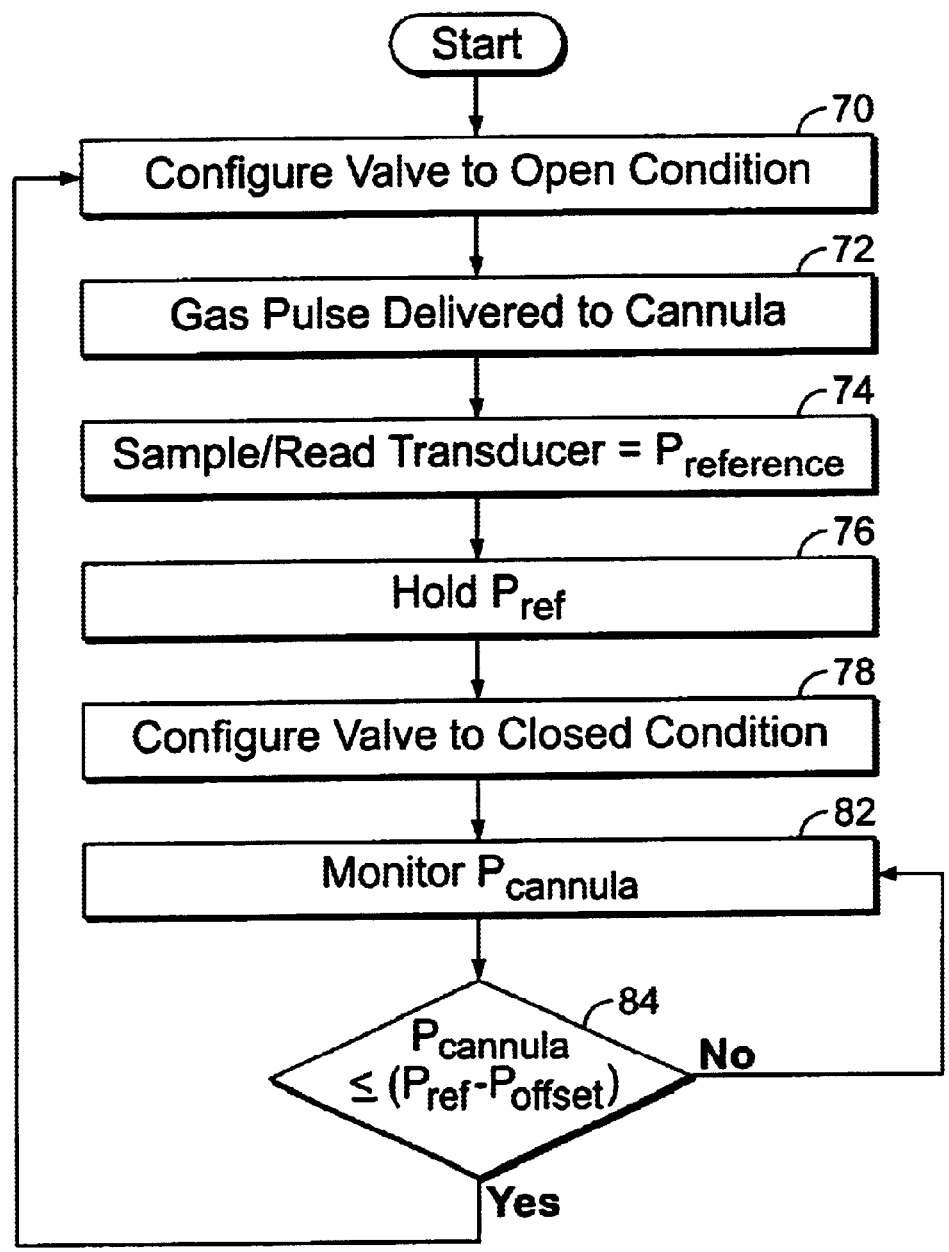
FIG. 3 is a flow chart illustrating the processing of the controller of the supplemental oxygen delivery system of FIGS. 1A and 1B.

The processing performed by the control system 36 of FIGS. 1A and 1B is illustrated in FIG. 3. When the system of FIGS. 1A and 1B is first turned on, valve 12 is configured in the open condition, as indicated at 70, and a gas pulse is delivered to the nasal cannula, as indicated at 72. As indicated at 74, with the valve in the open condition illustrated in FIG. 1B, the sample and hold circuit 44 samples or reads the pressure within line 28 via the pressure transducer 32. The sample and hold circuit may sample the pressure transducer for the entire time period that the valve is open (64 in FIG. 2), or wait until the very end of the time period. Early in the period of time that the valve 12 is open, the pressure in the line 28 may be high as some gas may enter it while the valve is opening. This pressure will be vented through the orifice 34 so that the pressure in line 28 near the end of the period of time that the valve is open will be at or very near atmospheric pressure.

As illustrated at 76 in FIG. 3, the pressure sensed by the pressure transducer, which is at or near atmospheric pressure, is held as the reference pressure ($P_{reference}$) by the sample and hold circuit 44 of control system 36 of FIGS. 1A and 1B.

As illustrated at 78, the control system then configures the valve to the closed condition, illustrated in FIG. 1A and, as indicated at 82, monitors the pressure within the nasal cannula 26 via the pressure transducer. The pressure within the cannula ($P_{cannula}$) is constantly compared to ($P_{reference} - P_{offset}$), as indicated at 84. Once $P_{cannula}$ drops below the predetermined pressure (which equals $P_{reference} - P_{offset}$) the valve 12 of FIGS. 1A and 1B is configured into the open condition, as indicated by 70 in FIG. 3. As a result, an oxygen pulse or dose is delivered to the cannula, and thus to the patient, as indicated at 72. The cycle then repeats with block 74 where the sample or read of the transducer occurs to provide the new $P_{reference}$ for the control system.

With reference to FIGS. 1A and 1B, the system 10 may be optionally equipped with an indicator light 90, preferably green in color, that is illuminated when the valve 12 is open and the system is delivering oxygen to the patient. In addition, the system may optionally include adjustable flow control valve 92 which may be manually adjusted by a user to increase the amount of oxygen delivered by the device as a pulse or dose.

Power for the system may be provided by batteries 94 so that the system of FIGS. 1A and 1B may be portable. Accordingly, the system may be provided with a second indicator light 96 (preferably red) which is illuminated by the control system to indicate that the battery charge level is low. Alternatively, light 90 may change in color from green to red when the battery is low (so that light 96 may be eliminated).

The supplemental oxygen delivery system of the present invention thus provides "on demand" delivery of oxygen to the patient and is self-calibrating so as to operate in a reliable and efficient fashion. The system is also economical to construct, maintain and operate as it does not require a second valve to perform the calibration. The omission of the second valve decreases construction and maintenance costs and increases battery life.

While the preferred embodiments of the invention have been shown and described, it will be apparent to those skilled in the art that changes and modifications may be made therein without departing from the spirit of the invention, the scope of which is defined by the appended claims.

What is claimed is:

1. A system for delivering supplemental gas to a patient comprising:

a. a source of pressurized gas;

b. a device for providing the gas to the patient;

c. a pressure transducer;

d. a transducer line in communication with the pressure transducer and an orifice that is continuously open to atmospheric pressure so that the pressure transducer is periodically exposed to atmospheric pressure via the orifice;

e. a valve in communication with the device for providing the gas to the patient and adjustable between an open condition where the source of pressurized gas is in communication with the device for providing the gas to the patient and a closed condition where the pressure transducer and transducer line are in communication with the device for providing the gas to the patient; and f. a controller in communication with the pressure transducer and the valve.

2. The system of claim 1 wherein the source of pressurized gas is a tank of oxygen.

3. The system of claim 2 wherein the tank is portable.

4. The system of claim 1 wherein the device for providing gas to the patient is a nasal cannula.

5. The system of claim 1 wherein the controller includes a sample and hold circuit.

6. The system of claim 1 wherein the controller includes a timer so that the valve may be configured in the open condition for a predetermined period of time.

7. The system of claim 1 wherein the valve is a solenoid valve.

8. The system of claim 1 wherein the orifice is formed in the transducer line.

9. The system of claim 1 further comprising a tee fitting in series communication with the transducer line, said tee fitting featuring the orifice.

10. The system of claim 1 where the orifice is approximately 0.010 inches in diameter.

11. A system for delivering supplemental gas to a patient comprising:

a. a source of pressurized gas;

b. a device for providing the gas to the patient;

c. a pressure transducer;

d. a transducer line in communication with the pressure transducer and an orifice that is open to atmospheric pressure;

e. a valve in communication with the device adapted to provide the gas to the patient and adjustable between an open condition where the source of pressurized gas is in communication with the device for providing the gas to the patient and a closed condition where the pressure transducer and transducer line are in communication with the device for providing the gas to the patient; and f. a controller in communication with the pressure transducer and the valve; whereby said pressure transducer senses a pressure in the transducer line when the valve is in the open condition and the sensed pressure is used by the controller as a reference pressure so that the valve is configured in the open condition by the controller when the pressure sensed by the pressure transducer drops to a predetermined pressure below the reference pressure when the valve is in the closed condition.

12. The system of claim 11 wherein the source of pressurized gas is a tank of oxygen.

13. The system of claim 12 wherein the tank is portable.

14. The system of claim 11 wherein the device for providing gas to the patient is a nasal cannula.

15. The system of claim 11 wherein the controller includes a sample and hold circuit for holding the reference pressure.

16. The system of claim 11 wherein the controller includes a timer so that the valve may be configured in the open condition for a predetermined period of time.

17. The system of claim 11 wherein the valve is a solenoid valve.

18. The system of claim 11 wherein the orifice is formed in the transducer line.

19. The system of claim 11 further comprising a tee fitting in series communication with the transducer line, said tee fitting featuring the orifice.

20. A method for calibrating a system for providing gas to a patient through a device, where the system has a controller, a pressure transducer and a single valve, comprising the steps of:

a. exposing the pressure transducer to atmospheric pressure when gas is being delivered to a patient by the system;

b. reading the atmospheric pressure from the pressure transducer via the controller;

c. storing the read pressure in the controller as a reference pressure;

d. exposing the pressure transducer to the device through which gas is provided to the patient when gas is not being provided to the patient; and e. opening the single valve of the system to deliver gas to the patient when the pressure in the device through which gas is provided to the patient drops to a predetermined pressure that is below the reference pressure.

* * * * *